(12) United States Patent
Woodward et al.

(10) Patent No.: US 7,868,035 B2
(45) Date of Patent: Jan. 11, 2011

(54) THERAPEUTIC ESTERS

(75) Inventors: David F. Woodward, Lake Forest, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 79 days.

(21) Appl. No.: 11/814,815

(22) PCT Filed: Jan. 31, 2006

(86) PCT No.: PCT/US2006/003363
§ 371 (c)(1),
(2), (4) Date: May 19, 2008

(87) PCT Pub. No.: WO2006/083841
PCT Pub. Date: Aug. 10, 2006

(65) Prior Publication Data
US 2009/0012145 A1    Jan. 8, 2009

Related U.S. Application Data

(60) Provisional application No. 60/649,378, filed on Feb. 1, 2005.

(51) Int. Cl.
*A61K 31/404* (2006.01)
*C07D 409/02* (2006.01)
(52) U.S. Cl. .................. 514/414; 514/415; 548/467
(58) Field of Classification Search ............... 514/414, 514/415; 548/467
See application file for complete search history.

(56) References Cited

U.S. PATENT DOCUMENTS 6,051,576 A    4/2000    Ashton et al.

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Bezuglov, et al., "Arachidonoylcholine and N,N-Dimethylaminoethyul Arachidonate, New Cholinergic Compounds," *Russian Journal of Bioorganic Chemistry*, 2001, vol. 27, No. 3, pp. 200-203.
Bezuglov, et al., "Bioactive Amides of Fatty Acids," *Biochemistry* (Moscow), 1998, vol. 63, No., pp. 22-30.
Bezuglov, et al., "Synthesis and Biological Evaluation of Novel Amides of Polyunsaturated Fatty Acids with Dopamine," *Bioorganic & Medicinal Chemistry Letters 11*, 2001, pp. 447-449.
Wartmann, et al., "The MAP Kinase Signal Transduction Pathway is Activated by the Endogenous Cannabinoid Anandamide," *FEBS Letters 359*, 1995, pp. 133-136.
Janusz, et al., "Vanilloids. 1. Analogs of Capsaicin with Antinociceptive and Antiinflammatory Activity," *J. Med. Chem.*, 1993, 36, pp. 2595-2604.
Bisogno, et al., "N-Acyl-Dopamines: Novel Synthetic CB$_1$ Cannabinoid-Receptor Ligands and Inhibitors of Anandamide Inactivation With Cannabimimetic Activity In Vitro and In Vivo," *Biochemical Society*, 2000, 351, pp. 817-824.
Bezuglov, et al., "Synthesis of Novel Coumarin-3-Carboxylic Acid Derivatives as Chemical Detectors of Hydroxyl Radicals in Biological Systems," *Russian Journal of Bioorganic Chemistry*, 1997, vol. 23, No. 4, pp. 288-291.
"Proposed Route to a PG-Serotonin Ester Combination," J-Star Research 2004.

* cited by examiner

*Primary Examiner*—Rebecca L Anderson
*Assistant Examiner*—Samantha L Shterengarts
(74) *Attorney, Agent, or Firm*—Kevin J. Forestal; John E. Wurst; Doina G. Ene

(57) ABSTRACT

A compound comprising

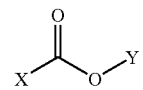

or a pharmaceutically acceptable salt or a prodrug thereof; wherein X and Y are described herein.

9 Claims, 1 Drawing Sheet

THERAPEUTIC ESTERS

Figure 1:
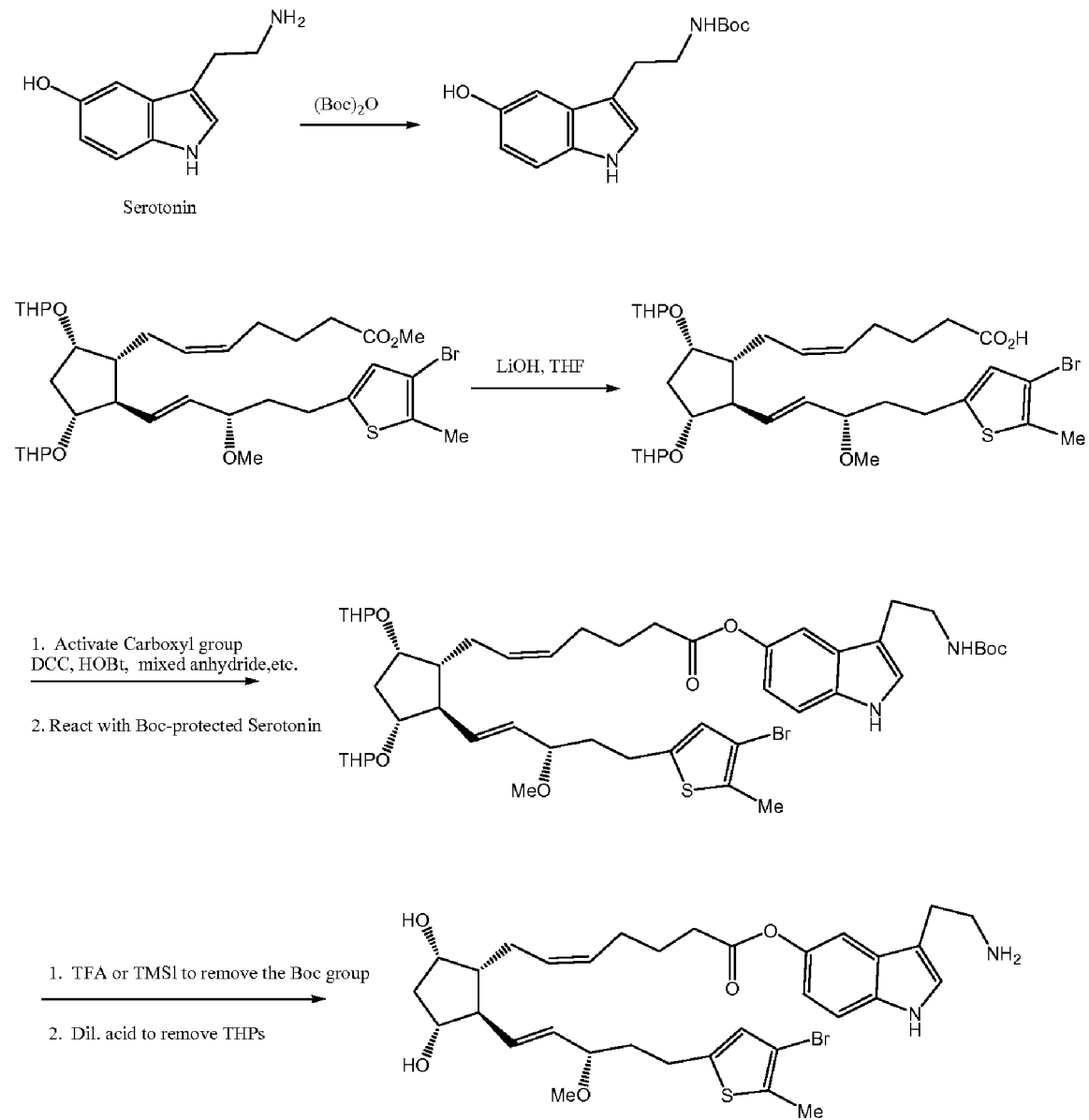

This is a national stage application under 35 U.S.C. §371 of PCT patent application PCT/US2006/003363, filed on Jan. 31, 2006, which claims the benefit of U.S. provisional patent application Ser. No. 60/649,378, filed Feb. 1, 2005, and each of which is incorporated by reference in their entirety.

DESCRIPTION OF RELATED ART

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

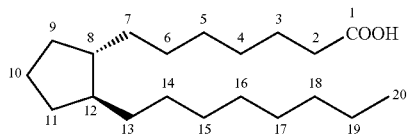

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Bezuglov et al (*Russian J. Bioorg. Chem.,* 2001, 27, 200-203) disclose esters of arachidonic acid and ethylene glycol, nitroethylene glycol, ascorbic acid, choline, and β-N,N-dimethylaminoethanol, as well as esters of docosahexaenoic acid and choline and β-N,N-dimethylaminoethanol.

U.S. Pat. No. 6,051,576 discloses an ester of prostaglandin $F_{2\alpha}$ and timolol.

BRIEF DESCRIPTION OF THE DRAWING FIGURES

FIG. 1 illustrates one method of preparing the compounds disclosed herein.

DETAILED DESCRIPTION OF THE INVENTION

Disclosed herein are compounds comprising

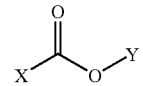

or pharmaceutically acceptable salts or prodrugs thereof; wherein X is linear hydrocarbyl having from 13 to 21 carbons, or X—$CO_2H$ has prostanoid activity; and Y—OH is a biogenic amine having greater than 5 carbon atoms.

Alternatively, X—$CO_2H$ is a linear carboxylic acid having from 14 to 22 carbons, or X—$CO_2H$ comprises B-Rg-A-$CO_2H$;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

Rg comprises a 5 or 6-membered carbocyclic or heterocyclic ring;

B is $CH_2$—$CH_2$—$CHOR^6R$, $CH$=$CH$—$CHOR^6R$, or $C$≡$C$—$CHOR^6R$; wherein $R^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms; Y—OH is a biogenic amine having greater than 5 carbon atoms; and wherein said compound is not an ester of prostaglandin $F_2$ and timolol.

Other compounds comprise

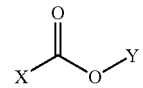

or a pharmaceutically acceptable salt or a prodrug thereof;

wherein X—$CO_2H$ has prostanoid activity or comprises B-Rg-A-$CO_2H$;

A is —$(CH_2)_6$—, cis —$CH_2CH=CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

Rg comprises a 5 or 6-membered carbocyclic or heterocyclic ring;

B is $CH_2$—$CH_2$—$CHOR^6R$, $CH=CH$—$CHOR^6R$, or $C\equiv C$—$CHOR^6R$; wherein $R^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine; and wherein said compound is not an ester of prostaglandin $F_2$ and timolol.

Methods, compositions, and medicaments, related to these compounds are also contemplated.

Hydrocarbyl has only carbon and hydrogen. Linear hydrocarbyl has no branching or rings. Thus, if X is linear hydrocarbyl, X—$CO_2H$ is a linear carboxylic acid. Linear carboxylic acids which have an even number of carbon atoms are fatty acids.

Saturated fatty acids have no C=C moieties and include, but are not limited to, myristic acid, palmitic acid, stearic acid, arachidic acid, and behenic acid.

Some fatty acids are unsaturated, these include, but are not limited to, the following:

monounsaturated fatty acids, which have one C=C group such as palmitoleic acid and oleic acid;

diunsaturated fatty acids, which have two C=C groups, such as linoleic acid;

triunsaturated fatty acids, which have three C=C groups, such as α-linolenic acid and γ-linolenic acid;

tetraunsaturated fatty acids, which have four C=C groups, such as arachidonic acid; and pentaunsaturated fatty acids, which have five C=C groups, such as eicosapentaenoic acid.

Some fatty acids have 14 carbon atoms such as myristic acid.

Some fatty acids have 16 carbon atoms such as palmitic and palmitoleic acid.

Some fatty acids have 18 carbon atoms such as stearic acid, oleic acid, linoleic acid, α-linolenic a, and γ-linolenic acid.

Some fatty acids have 20 carbon atoms such as eicosapentaenoic acid.

Thus, compounds, or pharmaceutically acceptable salts or prodrugs thereof, where X—$CO_2H$ belongs to any of the aforementioned fatty acids, or groups thereof, are specifically contemplated herein.

Prostanoid activity is broadly defined as any type of biological activity which a person of ordinary skill in the art reasonably believes is typical of a prostaglandin compound, which includes, but is not limited to, activity at a prostaglandin receptor in an in vivo assay. Alternatively, in vivo activity generally associated with prostagandins, such as reduction of intraocular pressure in a mammal, combined with a reasonable structural relationship to prostaglandins, is prostanoid activity. While not intending to be limiting, typical in vitro assays are presented herein. If there is conflicting data between assays, i.e. one assay indicates that a compound is a prostaglandin but another does not, the positive result is considered to define the compound for the purposes herein. Thus, activity in any assay or method acceptable to a person of ordinary skill in the art is sufficient to establish that a compound has prostanoid activity.

In one embodiment, X—$CO_2H$ is a natural prostaglandin. Natural prostaglandins include, but are not limited to:

Prostaglandin E, including prostaglandin $E_1$, prostaglandin $E_2$ and the like; and Prostaglandin F, including prostaglandin $F_{1\alpha}$, prostaglandin, $F_{2\alpha}$, and the like.

The term "biogenic amine" as used herein refers to broadly an amine or a quaternary ammonium salt which elicits a physiological response in a mammal. This physiological response may be a detectable response of a particular group of cells, organs, or tissues in a living mammal; or may be detectable in vitro in terms of binding, agonism, or antagonism of a particular receptor, or set of receptors, present in a mammal; or may be a response that is useful in treating or preventing an undesirable condition or disease in a mammal. While not intending to limit the overall scope of the invention in any way, examples of biogenic amines include cholinomimetics; antimuscarinics such as tropicamide; adrenergics such as epinephrine and isoprotenenol; dopaminergics, including dopamine; α-adrenoreceptor antagonists such as phentolamine; β-adrenergic antagonists such as timolol; β-adrenoceptor agonists such as salbutanol and salmeterol; monoamine oxidase inhibitors such as trancylpromine; serotonergics, including serotonin and analogs thereof; thyroid drugs such as thyroxine; and prodrugs and pharmaceutically acceptable salts of any of the above compounds or types of compounds. In certain embodiments, the biogenic amine is an amine selected from the group consisting of adrenergics, epinephrine, dopaminergics, dopamine, agonists of serotonin receptors, and serotonin.

In certain embodiments X—$CO_2H$ is B-Rg-A-$CO_2H$, wherein A is —$(CH_2)_6$—, cis —$CH_2CH=CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

Rg comprises a 5 or 6-membered carbocyclic or heterocyclic ring; and B is $CH_2$—$CH_2$—$CHOR^6R$, $CH=CH$—$CHOR^6R$, or $C\equiv C$—$CHOR^6R$; wherein $R^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms.

In relation to the identity of A disclosed in the chemical structures presented herein, in the broadest sense, A is —$(CH_2)_6$—, cis —$CH_2CH=CH$—$(CH_2)_3$— or —$CH_2C\equiv C$—$(CH_2)_3$—, wherein 1 or 2 carbon atoms may be substituted with S or O; or A is —$(CH_2)_n$—Ar—$(CH_2)_o$— wherein Ar is interarylene or heterointerarylene, the sum of m and o is from 1 to 4, and wherein one $CH_2$ may be substituted with S or O.

While not intending to be limiting, A may be —$(CH_2)_6$—, cis —$CH_2CH=CH$—$(CH_2)_3$—, or —$CH_2C\equiv C$—$(CH_2)_3$—.

Alternatively, A may be a group which is related to one of these three moieties in that any carbon is substituted with S and/or O. For example, while not intending to limit the scope of the invention in any way, A may be an S substituted moiety such as one of the following or the like.

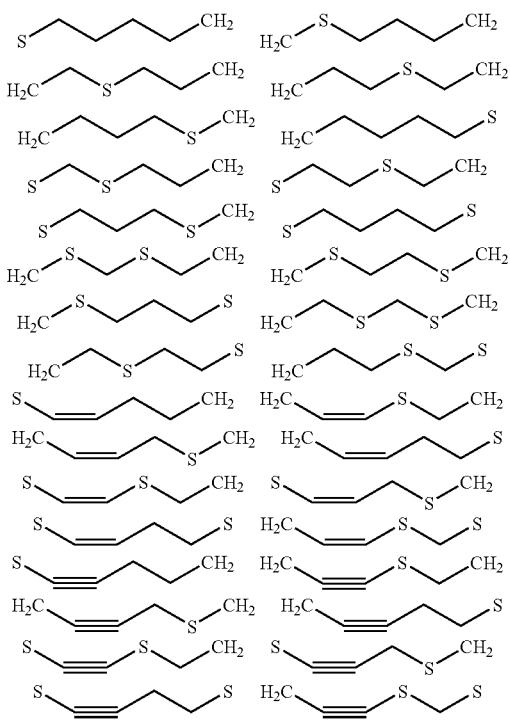

Alternatively, while not intending to limit the scope of the invention in any way, A may be an O substituted moiety such as one of the following or the like.

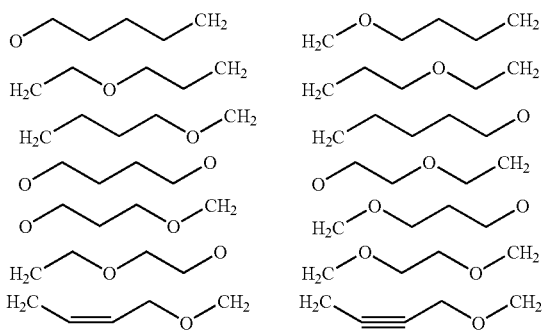

Alternatively, while not intending to limit the scope of the invention in any way, A may have both an O and an S substituted into the chain, such as one of the following or the like.

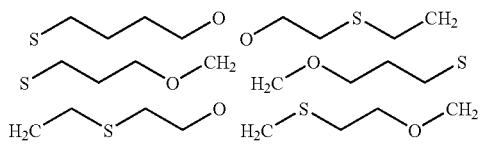

Alternatively, while not intending to limit the scope of the invention in any way, in certain embodiments A is —(CH$_2$)$_n$—Ar—(CH$_2$)$_o$— wherein Ar is interarylene or heterointerarylene, the sum of m and o is from 1 to 4, and wherein one CH$_2$ may be substituted with S or O. In other words, while not intending to limit the scope of the invention in any way, in one embodiment A comprises from 1 to 4 CH$_2$ moieties and Ar, e.g. —CH$_2$—Ar—, —(CH$_2$)$_2$—Ar—, —CH$_2$—ArCH$_2$—, —CH$_2$Ar(CH$_2$)$_2$—, —(CH$_2$)$_2$—Ar(CH$_2$)$_2$—, and the like; or A comprises O, from 0 to 3 CH$_2$ moieties, and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or A comprises S, from 0 to 3 CH$_2$ moieties, and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, and the like.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substitutents in addition to the two parts of the molecule it connects.

In one embodiment, Ar is substituted or unsubstituted interphenylene, interthienylene, interfurylene, or interpyridinylene. In another embodiment Ar is interphenylene (Ph). In another embodiment A is —(CH$_2$)$_2$-Ph-. While not intending to limit scope of the invention in any way, substituents may have 4 or less heavy atoms, or in other words, non hydrogen atoms. Any number of hydrogen atoms required for a particular substituent will also be included. Thus, the substituent may be hydrocarbyl having up to 4 carbon atoms, including alkyl up to C$_4$, alkenyl, alkynyl, and the like; hydrocarbyloxy up to C$_3$; CF$_3$; halo, such as F, Cl, or Br; hydroxyl; NH$_2$ and alkylamine functional groups up to C$_3$; other N or S containing substituents; and the like.

In one embodiment A is —(CH$_2$)$_m$—Ar—(CH$_2$)$_o$— wherein Ar is interphenylene, the sum of m and o is from 1 to 3, and wherein one CH$_2$ may be substituted with S or O.

In another embodiment A is —CH$_2$—Ar—OCH$_2$—. In another embodiment A is —CH$_2$—Ar—OCH$_2$— and Ar is interphenylene. In another embodiment, Ar is attached at the 1 and 3 positions, such as when A has the structure shown below.

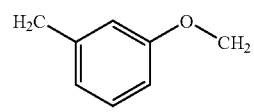

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph- wherein one CH$_2$ may be substituted with S or O.

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph-.

Thus, compounds such as the ones depicted below, or pharmaceutically acceptable salts or prodrugs thereof are possible.

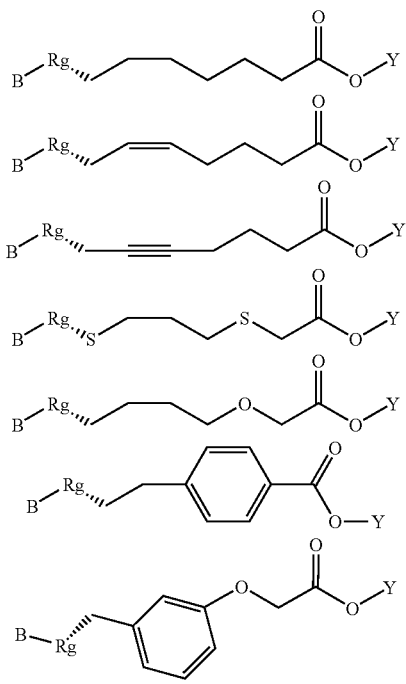

Rg comprises a 5 or 6-membered carbocycle or heterocyclic ring. A carbocyclic ring is an all-carbon ring, a heterocyclic ring contains both carbon and S, N, or O in the ring. Rg can also have any number of substituents other than A and B, up to as many as the ring will bear. In many cases, Rg has two substituents selected from the group consisting of OH, =O, Cl, F, Br, O-alkyl, CN, CO$_2$H, and CO$_2$-alkyl. Thus, compounds such as the ones depicted below are possible.

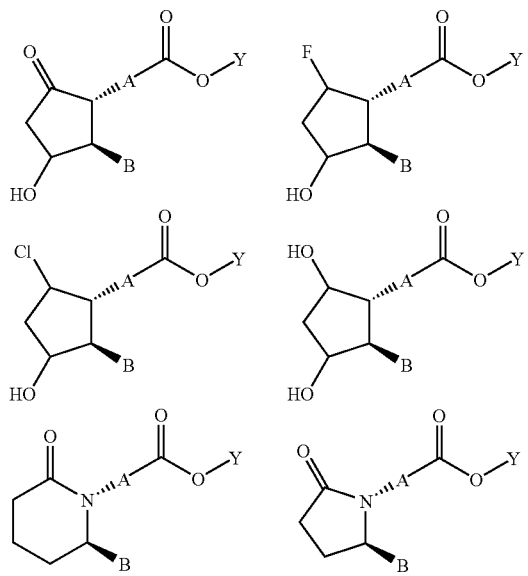

As mentioned above, B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms.

Alkyl is hydrocarbyl having no double or triple bonds including:

linear alkyl such as methyl, ethyl, propyl, n-butyl, n-pentyl, n-hexyl, and the like;

branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;

cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.

Heteroalkyl is alkyl having one or more carbon atoms substituted with O or S atoms, provided that no carbon has more than 1 covalent bond to O or S, i.e. there are no C=O, —O—CH$_2$—O—, —S—CH$_2$—S—, etc.; and that O and S are only bonded to carbon, i.e. there are no OH, SH, SO$_3$H, etc.

Aryl is an unsubstituted or substituted aromatic ring or ring system such as phenyl, naphthyl, biphenyl, and the like.

Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

Arylalkyl is alkyl which is substituted with aryl. In other words alkyl connects aryl to the remaining part of the molecule. Examples are —CH$_2$-Phenyl, —CH$_2$—CH$_2$-Phenyl, and the like.

Heteroarylalkyl is alkyl which is substituted with heteroaryl. In other words alkyl connects heteroaryl to the remaining part of the molecule. Examples are —CH$_2$-thienyl, —CH$_2$CH$_2$-benzothienyl, and the like.

Heteroarylheteroalkyl is heteroalkyl which is substituted with heteroaryl. In other words heteroalkyl connects heteroaryl to the remaining part of the molecule. Examples are —CH$_2$O-thienyl, —CH$_2$S-benzothienyl, and the like.

Arylheteroalkyl is heteroalkyl which is substituted with aryl. In other words heteroalkyl connects aryl to the remaining part of the molecule. Examples are —CH$_2$O-phenyl, —CH$_2$S-naphthyl, and the like.

Thus compounds such as the ones shown below are possible, or pharmaceutically acceptable salts or prodrugs thereof, where T is unsubstituted or substituted aryl or heteroaryl.

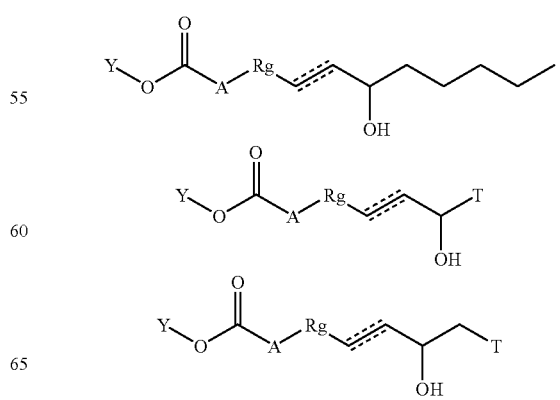

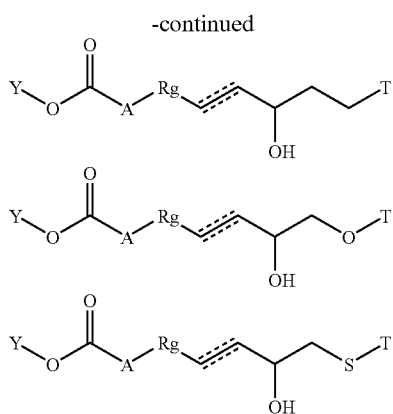

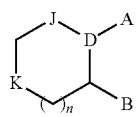

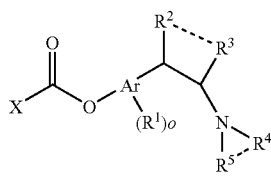

In certain embodiments R is n-butyl, $CH_2R^2$, $CH_2CH_2R^2$, $CH_2OR^2$, or $CH_2SR^2$, wherein $R^2$ is aryl or heteroaryl.

In other embodiments $R^2$ is substituted or unsubstituted phenyl, naphthyl, aryl, thienyl, or benzothienyl.

In other embodiments $R^2$ is phenyl, naphthyl, $CH_2$-(2-thienyl), $CH_2$-(3-thienyl), 2-thienyl, 3-thienyl, $CH_2$-(2-(3-chlorobenzothienyl)), $CH_2$-(3-benzothienyl), 2-(3-chlorobenzothienyl), or 3-benzothienyl.

In another embodiment $R^2$ is phenyl, naphthyl, 2-thienyl, 3-thienyl, 2-(3-chlorobenzothienyl), or 3-benzothienyl.

In other embodiments X comprises wherein J and K are independently C=O, CHOH, CHCl, CHF, or $CHOR^1$ wherein $R^1$ is $C_{1-6}$ alkyl;

D is N or CH; and n is 0 or 1.

Other compounds comprise or a pharmaceutically acceptable salt or a prodrug thereof;

wherein a dashed line represents the presence or absence of a bond;

$R^1$, $R^2$, $R^3$, $R^4$, and $R^5$ are independently, H, OH, O-alkyl having from 1 to 4 carbon atoms, alkyl having from 1 to 4 carbon atoms, phenyl, or pyridinyl;

Ar is phenyl or heteroaryl; and o is from 0 to 2.

Since $R^2$ and $R^3$ and $R^4$ and $R^5$ are connected by a dashed line, these moieties may form cyclic structures such that compounds such as the ones shown below are possible. Pharmaceutically acceptable salts and prodrugs thereof are also contemplated.

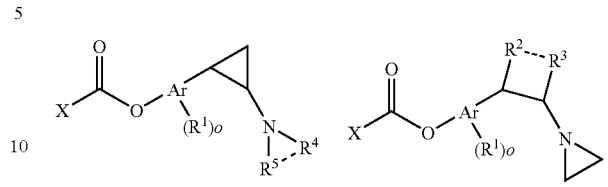

In certain compounds Ar is phenyl, imidazolyl, or indolyl.

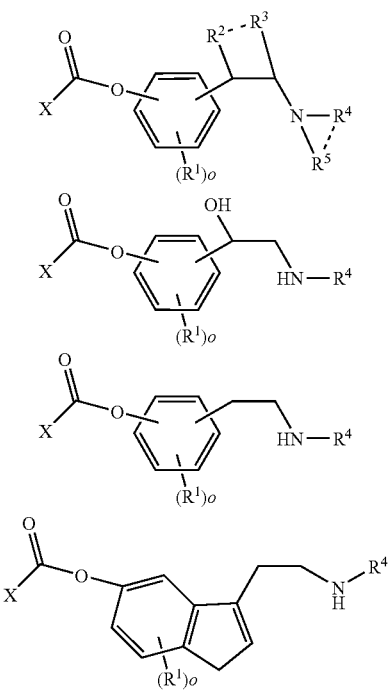

Pharmaceutically acceptable salts or prodrugs of compounds depicted by these structures are also contemplated.

Other compounds are depicted by the structures shown below. Pharmaceutically acceptable salts or prodrugs thereof are also contemplated.

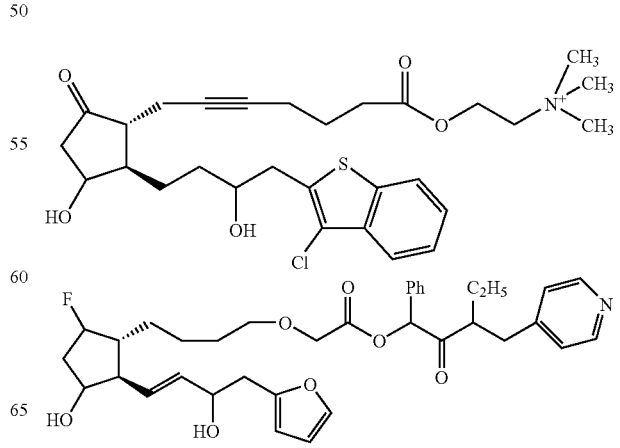

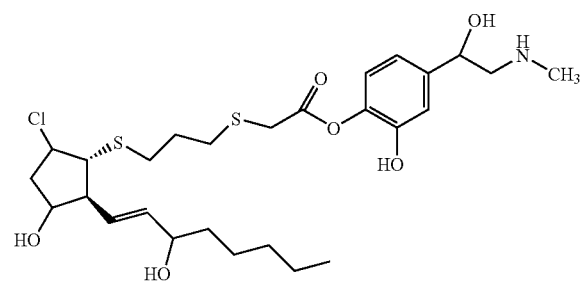
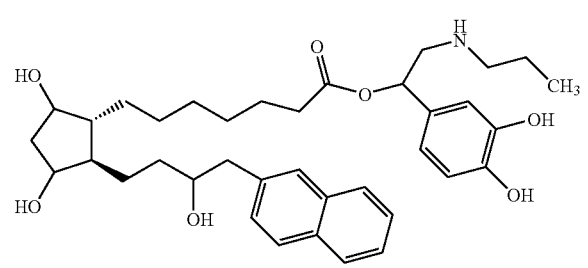
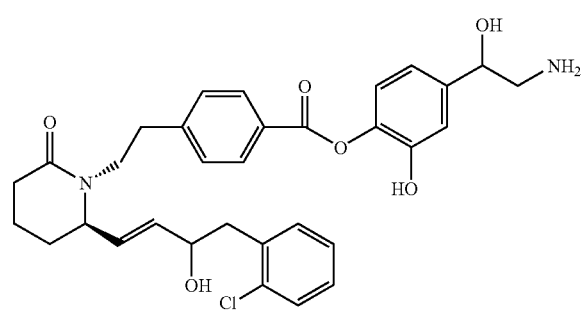
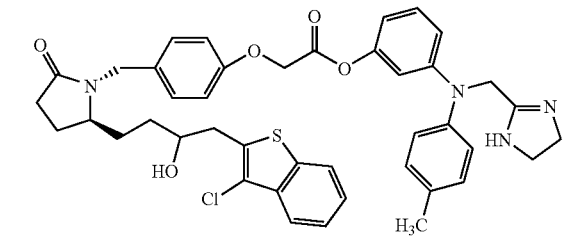
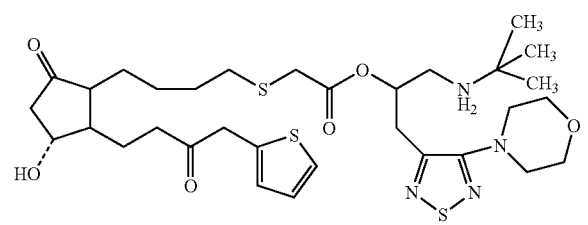
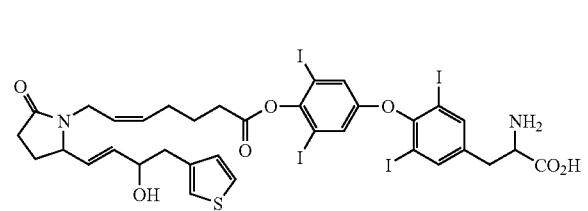
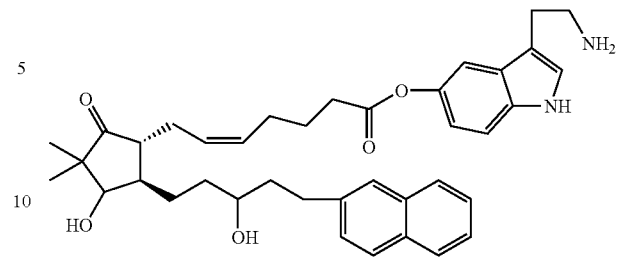
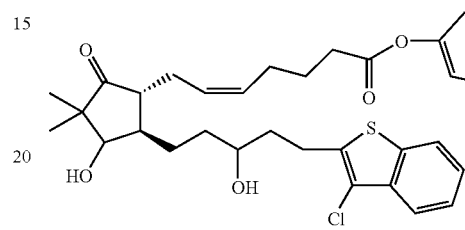
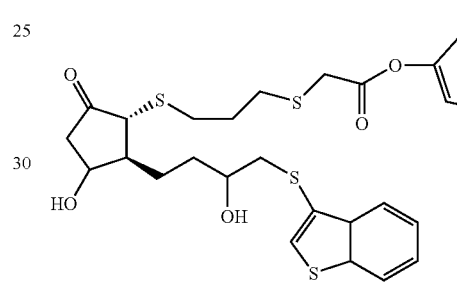
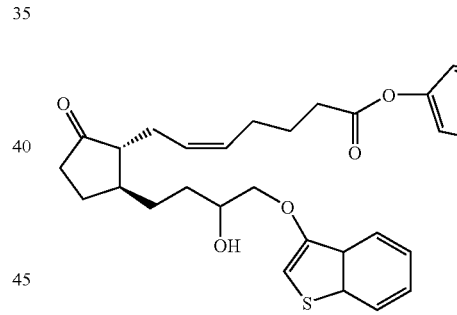
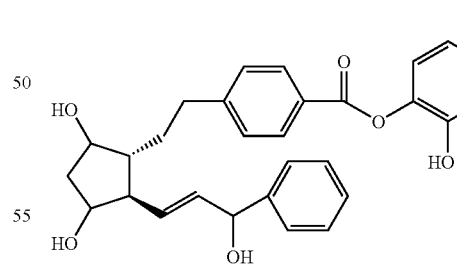
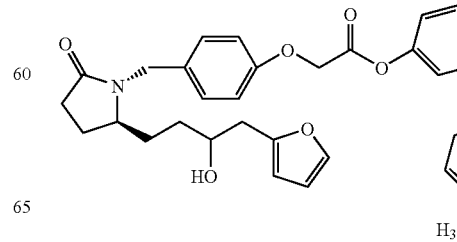

-continued

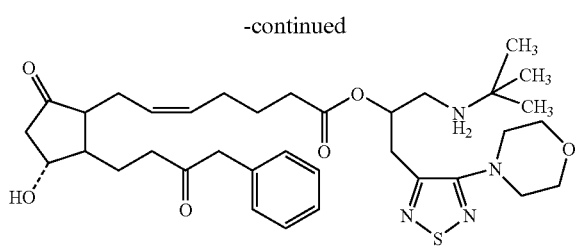

The compounds disclosed herein, in addition to being useful in reducing intraocular pressure for people with glaucoma or ocular hypertension, are also useful for the following:

Ocular Diseases: including treatment of non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions associated with photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, and retinitis pigmentosa; Dry eye, allergic conjunctivitis, and other ocular diseases;

Allergic and inflammatory disorders such as allergic conjunctivitis, rhinitis, dermatitis, and asthma;

Gastrointestinal disorders such as gastric or duodenal ulcer, inflammatory bowel disorder, Crohn's disease, ulcerative colitis, irritable bowel syndrome, constipation, and abdominal cramping;

Ob-Gyn disorders such as pre-term labor, dysmenorhoea, and related complications, CNS disorders such as depression, bipolar disorder, anxiety, attention deficit disorder, autism, obsessive-compulsive disorders, sleep disorders, Alzheimers disease, schizophrenia, and nausea and vomiting; and Movement disorders such as those associated with Parkinson's disease, Touret's syndrome, and multiple schlerosis.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |

-continued

| Ingredient | Amount (% w/v) |
| --- | --- |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci (www.ualberta.ca/~csps) 6 (1): 33-66, 2003 and Shareef et. al (AAPS PharmSci 2003; 5 (2) Article 17 (http://www.pharmsci.org)) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid humans in clinical trials for the treatment of irritable bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, markets pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

While not intending to limit the scope of the invention in any way, one possible methods of preparing the compounds disclosed is depicted in FIG. 1. In this method, a nitrogen of a biogenic amine such as serotonin having a hydroxyl group is protected using $(Boc)_2O$ or some other suitable reagent which selectively protects the amine functional group. A prostaglandin ester such as the one depicted in the FIGURE, where the hydroxyl groups are protected with THP, is hydrolyzed to the acid using LiOH or some other suitable reagent. The carboxylic acid is then activated using DCC, HOBt, a mixed anhydride or some other suitable reagent, and the activated acid is then reacted with the protected serotonin or other biogenic amine having a hydroxyl group. The protecting groups of the amine group are removed using TFA or TMSO if the amine is Boc protected, or another suitable reagent if a different protecting group is used. The protecting groups of the hydroxyl are then removed using dilute acid or another reagent appropriate for the removal of the protecting group.

Biological Activity

The activity of compounds disclosed herein is tested according to the following procedures. The results are presented in Table 1.

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors are washed with TME buffer, scraped from the bottom of the flasks, and homogenized for 30 sec using a Brinkman PT 10/35 polytron. TME buffer is added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate is centrifuged at 19000 r.p.m. for 20 min at 4° C. using a Beckman Ti-60 rotor. The resultant pellet is resuspended in TME buffer to give a final 1 mg/ml protein concentration, as determined by Biorad assay. Radioligand binding competition assays vs. [$^3$H-]17-phenyl $PGF_{2\alpha}$ (5 nM) are performed in a 100 μl volume for 60 min. Binding reactions are started by adding plasma membrane fraction. The reaction is terminated by the addition of 4 ml ice-cold TRIS-HCl buffer and rapid filtration through glass fiber GF/B filters using a Brandel cell harvester. The filters are washed 3 times with ice-cold buffer and oven dried for one hour. Non-specific binding is determined with 10 uM unlabeled 17-phenyl $PGF_{2\alpha}$.

[$^3$H-] $PGE_2$ (5 nM; specific activity 180 Ci mmol) is used as the radioligand for EP receptors. Binding studies employing $EP_1$, $EP_2$, $EP_3$, $EP_4$ are performed in duplicate in at least three separate experiments. A 200 μl assay volume is used. Incubations are for 60 min at 25° C. and are terminated by the addition of 4 ml of ice-cold 50 mM TRIS-HCl, followed by rapid filtration through Whatman GF/B filters and three additional 4 ml washes in a cell harvester (Brandel). Non-specific binding is determined with $10^{-5}$M of unlabeled $PGE_2$.

Methods for FLIPR™ Studies (a) Cell Culture

HEK-293 (EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), are cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells are seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells are then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates are washed four times with HBSS-HEPES buffer to remove excess dye leaving 100 μl in each well. Plates are re-equilibrated to 37° C. for a few minutes.

Cells are excited with an Argon laser at 488 nm, and emission is measured through a 510-570 nm bandwidth emission filter (FLIPR™, Molecular Devices, Sunnyvale, Calif.). Drug solution is added in a 50 μl volume to each well to give the desired final concentration. The peak increase in fluorescence intensity is recorded for each well. On each plate, four wells each serve as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hJP); U-46619 (hTP), depending on receptor). The peak fluorescence change in each drug-containing well is then expressed relative to the controls.

Compounds are tested in a high-throughput (HTS) or concentration-response (CoRe) format. In the HTS format, forty-four compounds per plate are examined in duplicates at a concentration of $10^{-5}$ M. To generate concentration-response curves, four compounds per plate are tested in duplicates in a concentration range between $10^{-5}$ and $10^{-11}$ M. The duplicate values are averaged. In either, HTS or CoRe format each compound is tested on at least 3 separate plates using cells from different passages to give an $n \geq 3$.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

One embodiment is use of a compound in the manufacture of a medicament for the treatment of glaucoma or ocular hypertension, said compound comprising

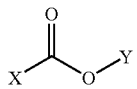

or a pharmaceutically acceptable salt or a prodrug thereof;

wherein X is linear hydrocarbyl having from 13 to 21 carbons, or X—$CO_2H$ has prostanoid activity;

Y—OH is a biogenic amine having greater than 5 carbon atoms; and wherein said compound is not an ester of prostaglandin $F_2$ and timolol.

In one embodiment X—$CO_2H$ is not arachidonic acid.

In another embodiment X—$CO_2H$ is a fatty acid.

In another embodiment X—$CO_2H$ is an unsaturated fatty acid having, 16 carbon atoms, 18 carbon atoms, or 20 carbon atoms.

In another embodiment X—$CO_2H$ is monounsaturated, diunsaturated, triunsaturated, tetraunsaturated, or pentaunsaturated.

In another embodiment X—$CO_2H$ is an unsaturated fatty acid.

In another embodiment X—$CO_2H$ has 16 carbon atoms.
In another embodiment X—$CO_2H$ has 18 carbon atoms.
In another embodiment X—$CO_2H$ has 20 carbon atoms.
In another embodiment X—$CO_2H$ is monounsaturated.
In another embodiment X—$CO_2H$ is diunsaturated.
In another embodiment X—$CO_2H$ is triunsaturated.
In another embodiment X—$CO_2H$ is tetraunsaturated.
In another embodiment X—$CO_2H$ is pentaunsaturated.
In another embodiment X is linear alkenyl or polyalkenyl.
In another embodiment X is linear alkyl.
In another embodiment X comprises from 17 to 20 carbon atoms.

In another embodiment Y—OH is a cholinomimetic, an antimuscarinic, an adrenergic, a dopaminergic, an α-adrenoceptor antagonist, a β-adrenergic antagonist, a serotonergic, serotonin, or a thyroid drug.

In another embodiment Y—OH is a cholinomimetic.
In another embodiment Y—OH is an antimuscarinic.
In another embodiment Y—OH is an adrenergic.
In another embodiment Y—OH is a dopaminergic.
In another embodiment Y—OH is an α-adrenoceptor antagonist.
In another embodiment Y—OH is a β-adrenergic antagonist.
In another embodiment Y—OH is a serotonergic.
In another embodiment Y—OH is serotonin.
In another embodiment Y—OH is a thyroid drug.

Another embodiment is use of a compound in the manufacture of a medicament for the treatment of glaucoma or ocular hypertension, said compound comprising

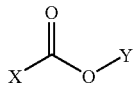

or a pharmaceutically acceptable salt or a prodrug thereof;

wherein X—$CO_2H$ is B-Rg-A-$CO_2H$, wherein A is —$(CH_2)_6$—, cis —$CH_2CH=CH—(CH_2)_3$—, or —$CH_2C≡C—(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

Rg comprises a 5 or 6-membered carbocyclic or heterocyclic ring; and

B is $CH_2$—$CH_2$—$CHOR^6R$, CH=CH—$CHOR^6R$, or C≡C—$CHOR^6R$; wherein $R^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine having greater than 5 carbon atoms; and wherein said compound is not an ester of prostaglandin $F_2$ and timolol.

In another embodiment X comprises

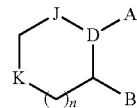

wherein J and K are independently C=O, CHOH, CHCl, CHF, or $CHOR^1$ wherein $R^1$ is $C_{1-6}$ alkyl;

D is N or CH; and n is 0 or 1.

In another embodiment R is n-butyl, $CH_2R^2$, $CH_2CH_2R^2$, $CH_2OR^2$, or $CH_2SR^2$, wherein $R^2$ is aryl or heteroaryl.

In another embodiment $R^2$ is substituted or unsubstituted phenyl, naphthyl, aryl, thienyl, or benzothienyl.

In another embodiment $R^2$ is phenyl, naphthyl, $CH_2$-(2-thienyl), $CH_2$-(3-thienyl), 2-thienyl, 3-thienyl, $CH_2$-(2-(3-chlorobenzothienyl)), $CH_2$-(3-benzothienyl), 2-(3-chlorobenzothienyl), or 3-benzothienyl.

In another embodiment $R^2$ is phenyl, naphthyl, 2-thienyl, 3-thienyl, 2-(3-chlorobenzothienyl), or 3-benzothienyl.

Another embodiment is use of a compound in the manufacture of a medicament for the treatment of glaucoma or ocular hypertension, said compound comprising

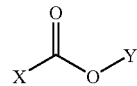

or a pharmaceutically acceptable salt or a prodrug thereof;

wherein X—$CO_2H$ is a linear carboxylic acid having from 14 to 22 carbons, or X—$CO_2H$ comprises B-Rg-A-$CO_2H$;

A is —$(CH_2)_6$—, cis —$CH_2CH=CH—(CH_2)_3$—, or —$CH_2C≡C—(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

Rg comprises a 5 or 6-membered carbocyclic or heterocyclic ring;

B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine having greater than 5 carbon atoms; and wherein said compound is not an ester of prostaglandin F$_2$ and timolol.

In another embodiment X—CO$_2$H is not arachidonic acid.

In another embodiment R$^6$ is H.

Another embodiment is use of a compound in the manufacture of a medicament for the treatment of glaucoma or ocular hypertension, said compound comprising

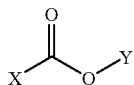

or a pharmaceutically acceptable salt or a prodrug thereof;

wherein X comprises

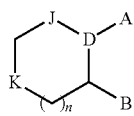

wherein J and K are independently C=O, CHOH, CHCl, CHF, or CHOR$^1$ wherein R$^1$ is C$_{1-6}$ alkyl;

D is N or CH;

n is 0 or 1;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine; and wherein said compound is not an ester of prostaglandin F$_2$ and timolol.

Another embodiment is use of a compound in the manufacture of a medicament for the treatment of glaucoma or ocular hypertension, said compound comprising

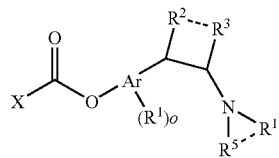

or a pharmaceutically acceptable salt or a prodrug thereof;

wherein a dashed line represents the presence or absence of a bond;

X—CO$_2$H is a linear carboxylic acid having from 14 to 22 carbons, or X—CO$_2$H comprises B-Rg-A-CO$_2$H;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

Rg comprises a 5 or 6-membered carbocyclic or heterocyclic ring;

B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms R$^1$, R$^2$, R$^3$, R$^4$, and R$^5$ five are independently, H, OH, O-alkyl having from 1 to 4 carbon atoms, alkyl having from 1 to 4 carbon atoms, phenyl, or pyridinyl;

Ar is phenyl or heteroaryl; and o is from 0 to 2.

In another embodiment X—CO$_2$H is not arachidonic acid.

In another embodiment Ar is phenyl, imidazolyl, or indolyl.

Another embodiment is use of a compound in the manufacture of a medicament for the treatment of glaucoma or ocular hypertension, said compound comprising

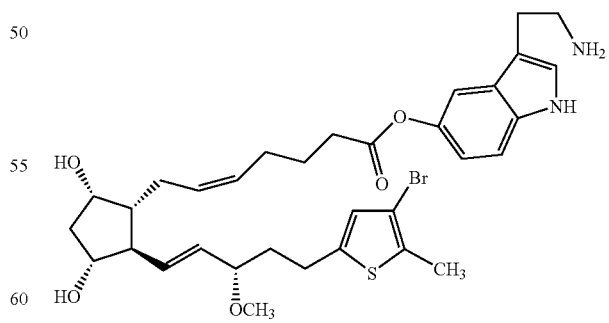

or a pharmaceutically acceptable salt or a prodrug thereof.

Another embodiment is use of a compound in the manufacture of a medicament for the treatment of glaucoma or ocular hypertension, said compound comprising

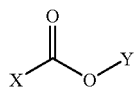

or a pharmaceutically acceptable salt or a prodrug thereof;

wherein X—CO$_2$H has prostanoid activity or comprises B-Rg-A-CO$_2$H;

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

Rg comprises a 5 or 6-membered carbocyclic or heterocyclic ring;

B is CH$_2$—CH$_2$—CHOR$^6$R, CH═CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine; and wherein said compound is not an ester of prostaglandin F$_{2\alpha}$ and timolol.

In another embodiment X comprises

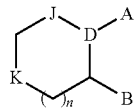

wherein J and K are independently C═O, CHOH, CHCl, CHF, or CHOR$^1$ wherein R$^1$ is C$_{1-6}$ alkyl;

D is N or CH; and n is 0 or 1.

One embodiment is a method comprising administering a compound to a mammal for the treatment of glaucoma or ocular hypertension, said compound comprising

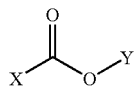

or a pharmaceutically acceptable salt or a prodrug thereof;

wherein X is linear hydrocarbyl having from 13 to 21 carbons, or X—CO$_2$H has prostanoid activity;

Y—OH is a biogenic amine having greater than 5 carbon atoms; and wherein said compound is not an ester of prostaglandin F$_2$ and timolol.

In another embodiment X—CO$_2$H is not arachidonic acid.

In another embodiment X—CO$_2$H is a fatty acid.

In another embodiment X—CO$_2$H is an unsaturated fatty acid having, 16 carbon atoms, 18 carbon atoms, or 20 carbon atoms.

In another embodiment X—CO$_2$H is monounsaturated, diunsaturated, triunsaturated, tetraunsaturated, or pentaunsaturated.

In another embodiment X—CO$_2$H is an unsaturated fatty acid.

In another embodiment X—CO$_2$H has 16 carbon atoms.

In another embodiment X—CO$_2$H has 18 carbon atoms.

In another embodiment X—CO$_2$H has 20 carbon atoms.

In another embodiment X—CO$_2$H is monounsaturated.

In another embodiment X—CO$_2$H is diunsaturated.

In another embodiment X—CO$_2$H is triunsaturated.

In another embodiment X—CO$_2$H is tetraunsaturated.

In another embodiment X—CO$_2$H is pentaunsaturated.

In another embodiment X is linear alkenyl or polyalkenyl.

In another embodiment X is linear alkyl.

In another embodiment X comprises from 17 to 20 carbon atoms.

In another embodiment Y—OH is a cholinomimetic, an antimuscarinic, an adrenergic, a dopaminergic, an α-adrenoceptor antagonist, a β-adrenergic antagonist, a serotonergic, serotonin, or a thyroid drug.

In another embodiment Y—OH is a cholinomimetic.

In another embodiment Y—OH is an antimuscarinic.

In another embodiment Y—OH is an adrenergic.

In another embodiment Y—OH is a dopaminergic.

In another embodiment Y—OH is an α-adrenoceptor antagonist.

In another embodiment Y—OH is a β-adrenergic antagonist.

In another embodiment Y—OH is a serotonergic.

In another embodiment Y—OH is serotonin.

In another embodiment Y—OH is a thyroid drug.

Another embodiment is a method comprising administering a compound to a mammal for the treatment of glaucoma or ocular hypertension, said compound comprising

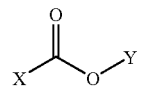

or a pharmaceutically acceptable salt or a prodrug thereof;

wherein X—CO$_2$H is B-Rg-A-CO$_2$H, wherein A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

Rg comprises a 5 or 6-membered carbocyclic or heterocyclic ring; and

B is CH$_2$—CH$_2$—CHOR$^6$R, CH═CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine having greater than 5 carbon atoms; and wherein said compound is not an ester of prostaglandin $F_{2\alpha}$ and timolol.

In another embodiment $X-CO_2H$ is not arachidonic acid.

In another embodiment X comprises

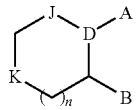

wherein J and K are independently C=O, CHOH, CHCl, CHF, or $CHOR^1$ wherein $R^1$ is $C_{1-6}$ alkyl;

D is N or CH; and n is 0 or 1.

In another embodiment R is n-butyl, $CH_2R^2$, $CH_2CH_2R^2$, $CH_2OR^2$, or $CH_2SR^2$, wherein $R^2$ is aryl or heteroaryl.

In another embodiment $R^2$ is substituted or unsubstituted phenyl, naphthyl, aryl, thienyl, or benzothienyl.

In another embodiment $R^2$ is phenyl, naphthyl, $CH_2$-(2-thienyl), $CH_2$-(3-thienyl), 2-thienyl, 3-thienyl, $CH_2$-(2-(3-chlorobenzothienyl)), $CH_2$-(3-benzothienyl), 2-(3-chlorobenzothienyl), or 3-benzothienyl.

In another embodiment $R^2$ is phenyl, naphthyl, 2-thienyl, 3-thienyl, 2-(3-chlorobenzothienyl), or 3-benzothienyl.

Another embodiment is a method comprising administering a compound to a mammal for the treatment of glaucoma or ocular hypertension, said compound comprising

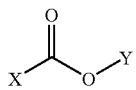

or a pharmaceutically acceptable salt or a prodrug thereof;

wherein $X-CO_2H$ is a linear carboxylic acid having from 14 to 22 carbons, or $X-CO_2H$ comprises $B-Rg-A-CO_2H$;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O;

Rg comprises a 5 or 6-membered carbocyclic or heterocyclic ring;

B is $CH_2-CH_2-CHOR^6R$, $CH=CH-CHOR^6R$, or $C\equiv C-CHOR^6R$; wherein $R^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine having greater than 5 carbon atoms; and wherein said compound is not an ester of prostaglandin $F_2$ and timolol.

In another embodiment $X-CO_2H$ is not arachidonic acid.

In another embodiment $R^6$ is H.

Another embodiment is a method comprising administering a compound to a mammal for the treatment of glaucoma or ocular hypertension, said compound comprising

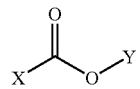

or a pharmaceutically acceptable salt or a prodrug thereof;

wherein X comprises

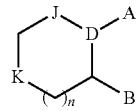

wherein J and K are independently C=O, CHOH, CHCl, CHF, or $CHOR^1$ wherein $R^1$ is $C_{1-6}$ alkyl;

D is N or CH;

n is 0 or 1;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O;

B is $CH_2-CH_2-CHOR^6R$, $CH=CH-CHOR^6R$, or $C\equiv C-CHOR^6R$; wherein $R^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms; and Y—OH is a biogenic amine; and wherein said compound is not an ester of prostaglandin $F_2$ and timolol.

Another embodiment is a method comprising administering a compound to a mammal for the treatment of glaucoma or ocular hypertension, said compound comprising

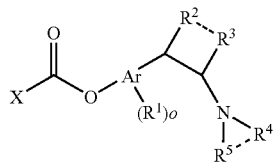

or a pharmaceutically acceptable salt or a prodrug thereof;

wherein a dashed line represents the presence or absence of a bond;

$X-CO_2H$ is a linear carboxylic acid having from 14 to 22 carbons, or $X-CO_2H$ comprises $B-Rg-A-CO_2H$;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O;

Rg comprises a 5 or 6-membered carbocyclic or heterocyclic ring;

B is $CH_2$—$CH_2$—$CHOR^6R$, $CH$=$CH$—$CHOR^6R$, or $C\equiv C$—$CHOR^6R$; wherein $R^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms $R^1$, $R^2$, $R^3$, $R^4$, and $R^5$ five are independently, H, OH, O-alkyl having from 1 to 4 carbon atoms, alkyl having from 1 to 4 carbon atoms, phenyl, or pyridinyl;

Ar is phenyl or heteroaryl; and o is from 0 to 2.

In another embodiment $X$—$CO_2H$ is not arachidonic acid.

In another embodiment Ar is phenyl, imidazolyl, or indolyl.

Another embodiment is a method comprising administering a compound to a mammal for the treatment of glaucoma or ocular hypertension, said compound comprising

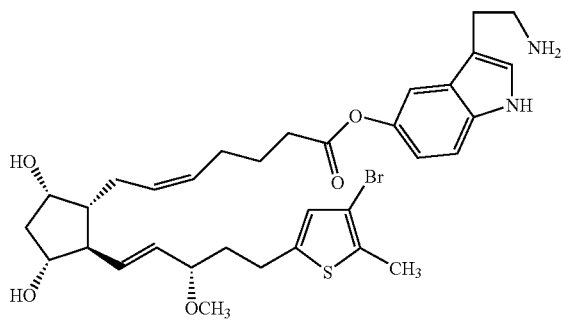

or a pharmaceutically acceptable salt or a prodrug thereof;

Another embodiment is a method comprising administering a compound to a mammal for the treatment of glaucoma or ocular hypertension, said compound comprising

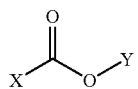

or a pharmaceutically acceptable salt or a prodrug thereof;

wherein $X$—$CO_2H$ has prostanoid activity or comprises B-Rg-A-$CO_2H$;

A is —$(CH_2)_6$—, cis —$CH_2CH$=$CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

Rg comprises a 5 or 6-membered carbocyclic or heterocyclic ring;

B is $CH_2$—$CH_2$—$CHOR^6R$, $CH$=$CH$—$CHOR^6R$, or $C\equiv C$—$CHOR^6R$; wherein $R^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine; and wherein said compound is not an ester of prostaglandin $F_{2\alpha}$ and timolol.

In another embodiment X comprises

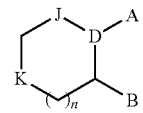

wherein J and K are independently C=O, CHOH, CHCl, CHF, or $CHOR^1$ wherein $R^1$ is $C_{1-6}$ alkyl;

D is N or CH; and n is 0 or 1.

One embodiment is a compound comprising

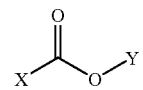

or a pharmaceutically acceptable salt or a prodrug thereof;

wherein X is linear hydrocarbyl having from 13 to 21 carbons, or X—$CO_2H$ has prostanoid activity;

Y—OH is a biogenic amine having greater than 5 carbon atoms; and wherein said compound is not an ester of prostaglandin $F_2$ and timolol.

In another embodiment X—$CO_2H$ is not arachidonic acid.

In another embodiment X—$CO_2H$ is a fatty acid.

In another embodiment X—$CO_2H$ is an unsaturated fatty acid having, 16 carbon atoms, 18 carbon atoms, or 20 carbon atoms.

In another embodiment X—$CO_2H$ is monounsaturated, diunsaturated, triunsaturated, tetraunsaturated, or pentaunsaturated.

In another embodiment X—$CO_2H$ is an unsaturated fatty acid.

In another embodiment X—$CO_2H$ has 16 carbon atoms.

In another embodiment X—$CO_2H$ has 18 carbon atoms.

In another embodiment X—$CO_2H$ has 20 carbon atoms.

In another embodiment X—$CO_2H$ is monounsaturated.

In another embodiment X—$CO_2H$ is diunsaturated.

In another embodiment X—$CO_2H$ is triunsaturated.

In another embodiment X—$CO_2H$ is tetraunsaturated.

In another embodiment X—$CO_2H$ is pentaunsaturated.

In another embodiment X is linear alkenyl or polyalkenyl.

In another embodiment X is linear alkyl.

In another embodiment X comprises from 17 to 20 carbon atoms.

In another embodiment Y—OH is a cholinomimetic, an antimuscarinic, an adrenergic, a dopaminergic, an α-adrenoceptor antagonist, a β-adrenergic antagonist, a serotonergic, serotonin, or a thyroid drug.

In another embodiment Y—OH is a cholinomimetic.
In another embodiment Y—OH is an antimuscarinic.
In another embodiment Y—OH is an adrenergic.
In another embodiment Y—OH is a dopaminergic.
In another embodiment Y—OH is an α-adrenoceptor antagonist.
In another embodiment Y—OH is a β-adrenergic antagonist.
In another embodiment Y—OH is a serotonergic.
In another embodiment Y—OH is serotonin.
In another embodiment Y—OH is a thyroid drug.

Another embodiment is a compound comprising

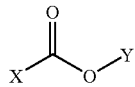

or a pharmaceutically acceptable salt or a prodrug thereof;

wherein X—CO$_2$H is B-Rg-A-CO$_2$H, wherein A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

Rg comprises a 5 or 6-membered carbocyclic or heterocyclic ring; and

B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine having greater than 5 carbon atoms; and wherein said compound is not an ester of prostaglandin F$_2$ and timolol.

In another embodiment X comprises

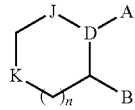

wherein J and K are independently C=O, CHOH, CHCl, CHF, or CHOR$^1$ wherein R$^1$ is C$_{1-6}$ alkyl;

D is N or CH; and n is 0 or 1.

In another embodiment R is n-butyl, CH$_2$R$^2$, CH$_2$CH$_2$R$^2$, CH$_2$OR$^2$, or CH$_2$SR$^2$, wherein R$^2$ is aryl or heteroaryl.

In another embodiment R$^2$ is substituted or unsubstituted phenyl, naphthyl, aryl, thienyl, or benzothienyl.

In another embodiment R$^2$ is phenyl, naphthyl, CH$_2$-(2-thienyl), CH$_2$-(3-thienyl), 2-thienyl, 3-thienyl, CH$_2$-(2-3-chlorobenzothienyl)), CH$_2$-(3-benzothienyl), 2-(3-chlorobenzothienyl), or 3-benzothienyl.

In another embodiment R$^2$ is phenyl, naphthyl, 2-thienyl, 3-thienyl, 2-(3-chlorobenzothienyl), or 3-benzothienyl.

Another embodiment is a compound comprising

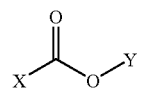

or a pharmaceutically acceptable salt or a prodrug thereof;

wherein X—CO$_2$H is a linear carboxylic acid having from 14 to 22 carbons, or X—CO$_2$H comprises B-Rg-A-CO$_2$H;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

Rg comprises a 5 or 6-membered carbocyclic or heterocyclic ring;

B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms; and Y—OH is a biogenic amine having greater than 5 carbon atoms; and wherein said compound is not an ester of prostaglandin F$_{2\alpha}$ and timolol.

In another embodiment X—CO$_2$H is not arachidonic acid.

In another embodiment R$^6$ is H.

Another embodiment is a compound comprising

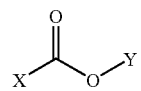

or a pharmaceutically acceptable salt or a prodrug thereof;

wherein X comprises

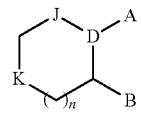

wherein J and K are independently C=O, CHOH, CHCl, CHF, or CHOR$^1$ wherein R$^1$ is C$_{1-6}$ alkyl;

D is N or CH;

n is 0 or 1;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine; and wherein said compound is not an ester of prostaglandin F$_{2\alpha}$ and timolol.

Another embodiment is a compound comprising

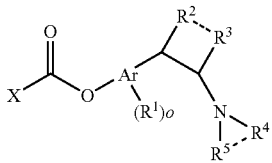

or a pharmaceutically acceptable salt or a prodrug thereof;

wherein a dashed line represents the presence or absence of a bond;

X—CO$_2$H is a linear carboxylic acid having from 14 to 22 carbons, or X—CO$_2$H comprises B-Rg-A-CO$_2$H;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

Rg comprises a 5 or 6-membered carbocyclic or heterocyclic ring;

B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms R$^1$, R$^2$, R$^3$, R$^4$, and R$^5$ five are independently, H, OH, O-alkyl having from 1 to 4 carbon atoms, alkyl having from 1 to 4 carbon atoms, phenyl, or pyridinyl;

Ar is phenyl or heteroaryl; and o is from 0 to 2.

In another embodiment X—CO$_2$H is not arachidonic acid.

In another embodiment Ar is phenyl, imidazolyl, or indolyl.

Another embodiment is a compound comprising

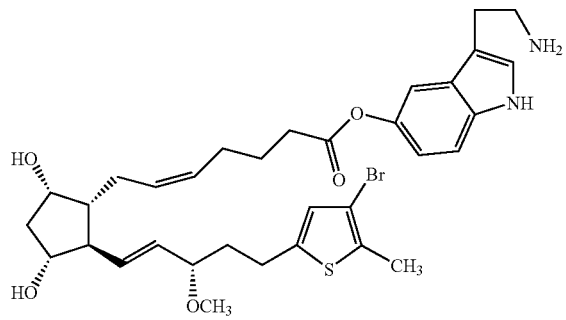

or a pharmaceutically acceptable salt or a prodrug thereof.

Another embodiment is a compound comprising

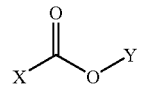

or a pharmaceutically acceptable salt or a prodrug thereof;

wherein X—CO$_2$H has prostanoid activity or comprises B-Rg-A-CO$_2$H;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

Rg comprises a 5 or 6-membered carbocyclic or heterocyclic ring;

B is CH$_2$—CH$_2$—CHOR$^6$R, CH=CH—CHOR$^6$R, or C≡C—CHOR$^6$R; wherein R$^6$ is H, methyl, or ethyl; and R is alkyl, aryl, heteroaryl, heteroalkyl, arylalkyl, heteroarylalkyl, heteroarylheteroalkyl, or arylheteroalkyl having from 1 to 12 carbon atoms;

Y—OH is a biogenic amine; and wherein said compound is not an ester of prostaglandin F$_{2\alpha}$ and timolol.

In another embodiment X comprises

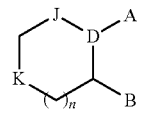

wherein J and K are independently C=O, CHOH, CHCl, CHF, or CHOR$^1$ wherein R$^1$ is C$_{1-6}$ alkyl;

D is N or CH; and n is 0 or 1.

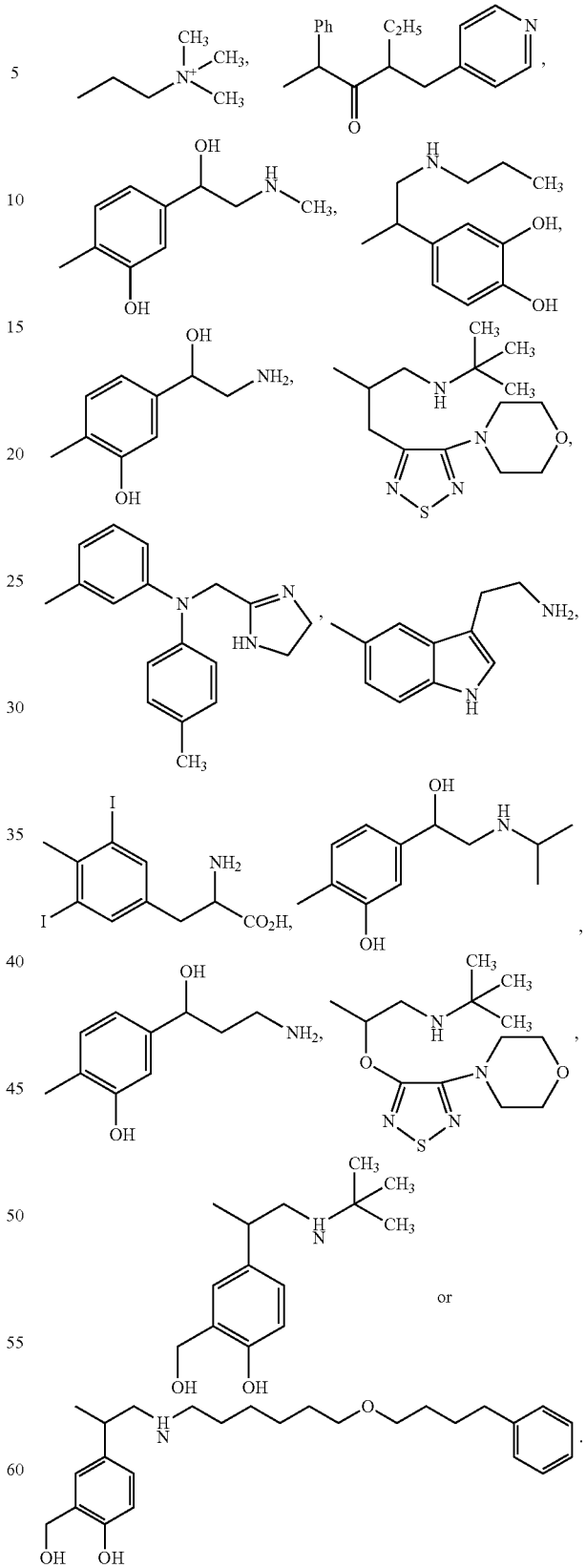

What is claimed is:

1. A compound represented by the formula:

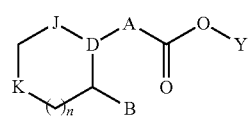

or a pharmaceutically acceptable salt thereof;
wherein J and K are independently C=O, CHOH, CHCl, CHF, or CHOR$^1$ wherein R$^1$ is C$_{1-6}$ alkyl;
D is N or CH;
n is 0 or 1;
A is —(CH$_2$)$_6$—, cis-CH$_2$CH=CH—(CH$_2$)$_3$—, or —CH$_2$C≡C—(CH$_2$)$_3$—, wherein 1 or 2 carbon atoms may be substituted with S or 0; or A is —(CH2)$_m$—Ar—(CH$_2$)$_o$—, wherein Ar is interarylene or heterointerarylene, the sum of m and o is from 1 to 4, and wherein one CH$_2$ may be substituted with S or 0;
B is CH$_2$—CH$_2$—CHOR$^6$R, CH=CH—CHOR$^6$R, or C≡C—CHOR$^6$R; wherein R$^6$ is H, methyl or ethyl; and R is alkyl, aryl, heteroaryl, heteroalkyl, arylalkyl, heteroarylalkyl, heteroarylheteroalkyl, or arylheteroalkyl having from 1 to 12 carbon atoms;
Y is a biogenic amine having greater than 5 carbon atoms selected from the group consisting of tropicamide, epinephrine, isoprotenenol, dopamine, phentolamine, timolol, salbutanol, salmeterol, trancylpromine, serotonin and thyroxine; and
wherein said compound is not an ester of prostaglandin F$_{2\alpha}$ and timolol.

2. The compound of claim 1 wherein
D is CH; and
n is 0.

3. The compound of claim 1 wherein R is n-butyl, CH$_2$R$^2$, CH$_2$CH$_2$CR$^2$, CH$_2$OR$^2$, or CH$_2$SR$^2$, wherein R$^2$ is aryl or heteroaryl.

4. The compound of claim 3 wherein R$^2$ is substituted or unsubstituted phenyl, naphthyl, aryl, thienyl, or benzothienyl.

5. The compound of claim 4 wherein R$^2$ is phenyl, naphthyl, 2-thienyl, 3-thienyl, 2-(3-chlorobenzothienyl), or 3-benzothienyl.

6. The compound of claim 1 wherein Y—OH is serotonin.

7. The compound of claim 4 comprising

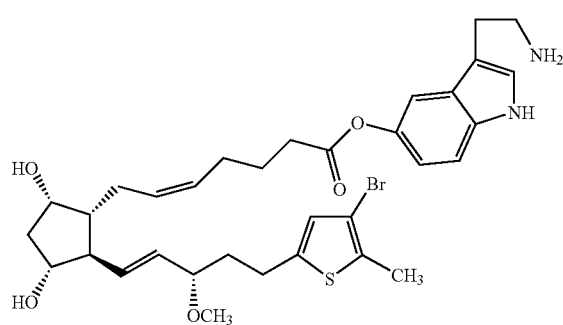

or a pharmaceutically acceptable salt or a prodrug thereof.

8. A method of treating glaucoma or ocular hypertension comprising administering a compound according to claim 1 to a mammal in need thereof.

9. The compound of claim 1 wherein Y is selected from